United States Patent [19]

Fellows et al.

[11] Patent Number: 4,886,913

[45] Date of Patent: Dec. 12, 1989

[54] PROCESS FOR PREPARING 2-METHYL-2-(METHYLTHIO) PROPIONALDEHYDE O-(METHYLCARBAMOYL) OXIME AS A WATER-WET CAKE

[75] Inventors: Constance A. Fellows, Durham; Patrick G. Hecht; Steven B. Levin, both of Raleigh, all of N.C.

[73] Assignee: Rhone-Poulenc Nederland, B.V., Amstelveen, Netherlands

[21] Appl. No.: 879,769

[22] Filed: Jun. 27, 1986

[51] Int. Cl.$^4$ ......................................... C07C 131/105
[52] U.S. Cl. .................................................. 564/255
[58] Field of Search ........................ 564/255; 514/477

[56] References Cited

U.S. PATENT DOCUMENTS

| | | | |
|---|---|---|---|
| 3,217,036 | 11/1965 | Payne | 564/268 |
| 3,217,037 | 11/1968 | Payne et al. | 564/268 |
| 3,506,698 | 4/1970 | Jelinek | 558/3 |
| 3,824,320 | 7/1974 | Buchanan | 514/477 |
| 4,097,526 | 6/1978 | Chan | 564/255 |

OTHER PUBLICATIONS

Saunders, J. H. et al., *Chem. Reviews*, vol. 43, (1948), pp. 207–211.

*Primary Examiner*—James H. Reamer
*Attorney, Agent, or Firm*—Morgan & Finnegan

[57] ABSTRACT

This invention relates to a process for preparing 2-methyl-2-(methylthio) propionaldehyde O-(methylcarbamoyl) oxime as an aqueous wet cake by reacting 2-methyl-2-(methylthio) propionaldehyde oxime with methyl isocyanate in the presence of an aqueous medium. This invention also relates to an aqueous wet cake composition containing 2-methyl-2-(methylthio) propionaldehyde O-(methylcarbamoyl) oxime.

18 Claims, No Drawings

PROCESS FOR PREPARING 2-METHYL-2-(METHYLTHIO) PROPIONALDEHYDE O-(METHYLCARBAMOYL) OXIME AS A WATER-WET CAKE

BRIEF SUMMARY OF THE INVENTION

1. Technical Field

This invention relates to a process for preparing 2-methyl-2-(methylthio) propionaldehyde O-(methylcarbamoyl) oxime (aldicarb) as an aqeuous wet cake by reacting 2-methyl-2-(methylthio) propionaldehyde oxime (aldicarb oxime) with methyl isocyanate in an aqueous medium. This invention also relates to an aqueous wet cake composition containing 2-methyl-2-(methylthio) propionaldehyde O-(methylcarbamoyl) oxime.

2. Background of the Invention

The carbamoylation reaction of an oxime compound with an isocyanate compound in an organic solvent such as dichloromethane is known and practiced in the art.

U.S. Pat. No. 3,217,037 describes a process for preparing 2-hydrocarbylthio-sulfinyl and sulfonylalkanal carbamoyloximes including 2-methyl-2-(methylthio) propionaldehyde O-(methylcarbamoyl) oxime which involves reacting an oxime compound with an isocyanate compound in an inert organic solvent. The inert organic solvents described in the patent which can be employed are those inert to isocyanates in general, i.e., those free of radicals such as hydroxy or amine radicals. Illustrative solvents described in the patent are aliphatic and aromatic hydrocarbons such as hexane, heptane, octane, benzene, toluene and the like, and ethers such as diethyl ether, ethyl propyl ether and the like.

U.S. Pat. No. 3,506,698 describes a process for preparing thiolhydroxamate carbamates which involves the reaction of thiolhydroxamate esters such as methyl thiolacetohydroxamate esters with a carbamylating agent such as isocyanic acid or its methyl ester in an aqueous medium at a temperature of between 0° C. and the boiling point of the reaction mass to obtain the corresponding thiolhydroxamate carbamates. At column 1, lines 58-60 of this patent, it is pointed out that thiolhydroxamates are not oximes.

It is therefore an object of this invention to provide a process for preparing 2-methyl-2-(methylthio) propionaldehyde O-(methylcarbamoyl) oxime by reacting 2-methyl-2-(methylthio) propionaldehyde oxime with methyl isocyanate in an aqueous medium, and thereby eliminating the need for organic solvents. It is another object of this invention to provide a water-wet cake composition containing 2-methyl-2-(methylthio) propionaldehyde O-(methylcarbamoyl) oxime.

DISCLOSURE OF THE INVENTION

This invention relates to a process for preparing 2-methyl-2-(methylthio) propionaldehyde O-(methylcarbamoyl) oxime by reacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime. This invention further relates to a water-wet cake composition containing 2-methyl-2-(methylthio) propionaldehyde O-(methylcarbamoyl) oxime.

DETAILED DESCRIPTION

As stated above, the process for this invention is carried out in the presence of water rather than an organic solvent. This is a significant discovery for several reasons. The use of water provides for increased safety in comparison with certain organic solvents which may exhibit toxic properties or pose other health and safety hazards. In addition, the use of water avoids any adverse environmental aspects such as air and water pollution which may be associated with certain organic solvents. Further, in comparison with certain orgnic solvents, the use of water is economically advantageous in that is is inexpensive and no recycle is necessary.

The process of this invention can be carried out by contacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime as a solid in an aqueous slurry which is then filtered to give a water-wet cake.

2-Methyl-2-(methylthio) propionaldehyde oxime is a known material which can be prepared according to the procedure described in U.S. Pat. No. 3,217,036. Methyl isocyanate is a known material which can be prepared by conventional methods. 2-Methyl-2-(methylthio) propionaldehyde O-(methylcarbamoyl) oxime is a known material which is the active ingredient in various TEMIK ® brand aldicarb pesticides available from Union Carbide Agricultural Products Comapny, Inc., Research Triangle Park, N.C.

The amount of 2-methyl-2-(methylthio) propionaldehyde oxime and methyl isocyanate used in the process of this invention can vary over a wide range. In general, the molar ratio of methyl isocyanate to 2-methyl-2-(methylthio) propionaldehyde oxime can range from about 0.25:1 to about 2:1. Preferably, an equimolar amount or slight excess of methyl isocyanate is employed to ensure that 2-methyl-2-(methylthio) propionaldehyde oxime is completely reacted.

The amount of water used in the process of this invention is not narrowly critical and can vary over a wide range. In general, the molar ratio of 2-methyl-2-(methylthio) propionaldehyde oxime to water can range from about 1:1 or less to about 1:50 or greater, preferably from about 1:10 to about 1:40. The amount of water used in the process of this invention is in general influenced primarily by reaction equipment including heat removal capability and solids handling capability.

A catalyst can optionally be used in the process of this invention to facilitate the carbamoylation reaction. Suitable catalysts include a tertiary amine or an organotin catalyst. Other suitable catalysts include alkali metal and alkaline earth metal oxides, carbonates, bicarbonates or basic ion exchangers and carboxylic acid derivative salts. Illustrative tertiary amine catalysts include, for example, triethylamine, trimethylamine and the like. Illustrative organotin catalysts include, for example, dibutyltin diacetate, dibutyltin dichloride, dibutyltin dimethoxide, dibutyltin dilaurate, dibutyltin maleate, dibutyltin di-2-ethylhexenoate, stannous octanoate, stannous oleate and the like. Such catalysts are conventional materials known in the art.

The amount of catalyst which can be used in the process of this invention is a catalytically effective amount and can vary over a wide range. Generally, the amount of catalyst employed can range from about 0.01 weight percent to about 1.0 weight percent or higher based on the total weight of methyl isocyanate and 2-methyl-2-(methylthio) propionaldehyde oxime.

The reaction temperature is not critical and can be varied over a wide range. The process of this invention is normally conducted at a temperature in the range of from about 0° C. to about 30° C., preferably from about 5° C. to about 25° C. The reaction temperature is in general limited primarily by physical constraints such as vaporization or freezing of the reactants or other ingredients. At temperatures below about 0° C., 2-methyl-2-(methylthio) propionaldehyde oxime tends to freeze out while the temperatures in excess of about 30° C. the reaction of methyl isocyanate with water is favored over the reaction of methyl isocyanate with 2-methyl-2-(methylthio) propionaldehyde oxime. The reaction of methyl isocyanate with 2-methyl-2-(methylthio) propionaldehyde oxime proceeds significantly faster than the reaction of methyl isocyanate with water at temperatures from about 0° C. to about 30° C.

Reaction pressures are not critical. The process of this invention can be conducted at either subatmospheric, atmospheric or superatmospheric pressure. For convenience, the reaction is usually conducted at atmospheric or autogenous pressure.

The reaction time period is not narrowly critical and can vary from second(s) or instantaneous to as long as several hours. The process of this invention is effected over a period of time sufficient to produce 2-methyl-2-(methylthio) propionaldehyde O-(methylcarbamoyl) oxime. Generally, when operating in the preferred temperature range, reaction times of from about one-half hour or less to about 4 hours are sufficient to complete the reaction of methyl isocyanate with 2-methyl-2-(methylthio) propionaldehyde oxime. Reaction time is influenced by the reaction temperature, the concentration and choice of catalyst and other factors known to those skilled in the art.

The process of this invention can be conducted by mixing 2-methyl-2-(methylthio) propionaldehyde oxime with water at a temperature of from about 0° C. to about 30° C. after which a catalyst is optionally added to the mixture. While maintaining the reaction temperature between about 0° C. and 30° C., methyl isocyanate is added with vigorous stirring over a sufficient period of time to provide for substantially complete conversion of 2-methyl-2-(methylthio) propionaldehyde oxime to 2-methyl-2-(methylthio) propionaldehyde O-(methylcarbamoyl) oxime as a solid in aqueous slurry which is then filtered to give a water-wet cake. The process of this invention can provide 2-methyl-2-(methylthio) propion-aldehyde O-(methylcarbamoyl) oxime on a yield basis in excess of 90 percent based on the weight of 2-methyl-2-(methylthio) propionaldehyde oxime.

The methyl isocyanate addition period can range from seconds to hours or longer, and can occur over one, two or even more separate addition periods, i.e., batchwise, continuously or intermittently introduced into the reaction mixture. Generally, the methyl isocyanate addition period can range from about one-half hour or less to about 2 hours or longer depending upon the amount of 2-methyl-2-(methylthio) propionaldehyde oxime and catalyst employed in the process and the ability to control the reaction temperature. The stirring period can also range from seconds to hours or longer and can be approximately co-extensive with the methyl isocyanate addition period. However, the stirring period is generally longer than the methyl isocyanate addition period in order to effect substantially complete conversion of 2-methyl-2-(methylthio) propionaldehyde oxime to 2-methyl-2-(methylthio) propionaldehyde O-(methylcarbamoyl) oxime.

Other ingredients can optionally be employed in the process of this invention. An organic or inorganic acid can be used to quench the reaction (tie up the catalyst and raise the reaction pH to about 4 or 5) and also provide additional stability to the water-wet cake product. Suitable organic and inorganic acids include phosphoric acid, hydrochloric acid, sulfuric acid, acetic acid and the like. The amount of acid which can be employed is not narrowly critical and is dependent upon the amount of catalyst and reactants used in the process. The amount of acid can range from 0.0001 weight percent or less to about 1.0 weight percent or greater based on the weight of the entire reaction mass.

Antifoaming agents and surfactants can optionally be employed in the process of this invention. Such antifoaming agents and surfactants are conventional materials known in the art. Suitable antifoaming agents include, for example, SAG 10 and SAG 30 which are available from Union Carbide Corporation, Danbury, Conn. and Q-132, which is available from SWS Silicones Corporation, Adrian, Mich. Suitable surfactants include conventional ionic and nonionic materials such as Tergitol 15-S7 available from Union Carbide Corporation, Danbury, Conn. and Pluronic L-61 and L-101 available from BASF. The amount of antifoaming agent and surfactant employed in the process of this invention can range from about 0.0001 weight percent or less to about 1.0 weight percent (based on the weight of the entire reaction mass) or greater for each ingredient.

The process of this invention can be conducted in a batch, semicontinuous or continuous fashion. The reaction can be conducted in a single reaction zone or in a plurality of reaction zones, in series or in parallel or it may be conducted intermittently or continuously in an elongated tubular zone or series of such zones. The materials of construction employed should be inert to the reactants during the reaction and the fabrication of the equipment should be able to withstand the reaction temperatures and pressure. Means to introduce and/or adjust the quantity of reactants or ingredients introduced, either intermittenly or continuously into the reaction zone during the course of the reaction can be conveniently utilized in the process especially to maintain the desired molar ratio of the reactants.

The process is preferably conducted in either glass lined, stainless steel or similar type reaction equipment. The reaction zone can be fitted with one or more internal and/or external heat exchanger(s) in order to control undue temperature fluctuations, or to prevent any possible "runaway" reaction temperatures. In preferred embodiments of the process, agitation means to vary the degree of mixing the reaction mixtures can be employed. Mixing by vibration, shaking, stirring, rotation, oscillation, ultrasonic vibration or the like are all illustrative of the types of agitation means contemplated. Such means are available and well known to those skilled in the art.

As stated above, a water-wet cake product is prepared by the process of this invention. The water-wet cake product generally contains from about 70 weight percent to about 95 weight percent or greater of 2-methyl-2-(methylthio) propionaldehyde O-(methylcarbamoyl) oxime, less than about 0.1 weight percent to about 15 weight percent of residual 2-methyl-2-(methylthio) propionaldehyde oxime and from about 5 weight percent or less to about 30 weight percent of water (weight percent based on the total weight of the product). Amounts of water greater than about 30 weight percent tend to provide a slurry product rather than a water-wet cake product. Other ingredients such as an organic or inorganic acid, an antifoaming agent and a surfactant as described above and certain impurities, e.g., methacrolein oxime carbamate, can be present in the water-wet cake product in minor amounts, e.g., individual amounts from about 0.0001 weight percent or less to about 1 weight percent.

The water-wet cake product prepared by the process of this invention is useful in formulating various TEMIK ® brand aldicarb pesticides available from Union Carbide Agricultural Products Company, Inc., Research Triangle Park, N.C.

The following examples are illustrative of the process of this invention.

EXAMPLE 1

Into a one liter glass resin kettle equipped with an air-driven stirrer, a pressure-equalizing dropping funnel with Teflon ® tube for subsurface addition, a thermometer and a dry ice/acetone cold condenser was added 66.5 grams (0.50 mole) of 2-methyl-2-(methylthio) propionaldehyde oxime (aldicarb oxime) and 266 milliliters of water. After cooling the mixture to a temperature of 5° C. with a water/salt/ice bath, 0.52 grams (0.005 mole) of triethylamine was added to the kettle under a nitrogen atmosphere. A stoichiometric amount of methyl isocyanate (29.5 milliliters, 0.50 mole) was then added over a period of 30 minutes at a temperature of 5° C.–10° C. with vigorous stirring. The water/salt/ice bath was removed and the mixture was stirred for an additional 60 minutes at a temperature of 15° C.–20° C. after which an additional 2.0 milliliters (0.03 mole) of methyl isocyanate was added and the mixture stirred for an additional period of 30 minutes. The water/salt/ice bath was then put back in place and 2.9 grams of phosphoric acid in 10 milliliters of water was added in a slow stream subsurface. The resulting solid product was filtered off on a sintered glass funnel to give 107.1 grams (wet weight) of a fluffy white powder. High pressure liquid chromatographic analysis (internal standard) indicated the following: 76.00 percent 2-methyl-2-(methylthio) propionaldehyde O-(methylcarbamoyl) oxime (aldicarb) (89 percent yield based on aldicarb oxime) and 0.36 percent 2-methyl-2-(methylthio) propionaldehyde oxime (aldicarb oxime); 23.64 percent water content was determined by Karl Fischer titration.

EXAMPLE 2

Into a one liter glass resin kettle equipped with a metal pitched-blade agitator, a pressure-equalizing dropping funnel with Teflon ® tube for subsurface addition, a thermometer and a dry ice/acetone cooled condenser was added 66.5 grams (0.50 mole) of 2-methyl-2-(methylthio) propionaldehyde oxime and 112 milliliters of water. After cooling the mixture to a temperature of 2° C.–3° C. with a water/salt/ice bath, 0.52 grams (0.005 mole) of triethylamine was added to the kettle under a nitrogen atmosphere. A stoichiometric amount of methyl isocyanate (29.5 milliliters, 0.50 mole) was then added over a period of 30 minutes at a temperature of 4° C.–14° C. with vigorous stirring. The water/salt/ice bath was removed and the mixture was stirred for an additional 75 minutes at a temperature of 10° C.–18° C. after which an additional 2.0 milliliters (0.03 mole) of methyl isocyanate was added and the mixture stirred for an additional period of 30 minutes. The water/salt/ice bath was then put back in place and 2.9 grams of phosphoric acid in 10 milliliters of water was added in a slow stream subsurface. The resulting solid product was filtered off on a sintered glass funnel and rinsed with hexane to give 104.4 grams (wet weight) of a fluffy white powder. High pressure liquid chromatographic analysis (internal standard) indicated the following: 84.00 percent 2-methyl-2-(methylthio) propionaldehyde O-(methylcarbamoyl) oxime (89.1 percent yield based on aldicarb oxime) and 2.38 percent 2-methyl-2-(methylthio) propionaldehyde oxime; 13.62 percent water content was determined by Karl Fischer titration.

EXAMPLE 3

Into a one liter glass resin kettle equipped with an air-driven stirrer, a pressure-equalizing dropping funnel with Teflon ® tube for subsurface addition, a thermometer and a dry ice/acetone cooled condenser was added 66.5 grams (0.50 mole) of 2-methyl-2-(methylthio) propionaldehyde oxime and 266 milliliters of water. After the mixture was cooled to a temperature of 5° C. with a salt/water/ice bath, 0.52 grams (0.005 mole) of triethylamine was added to the kettle under a nitrogen atmosphere. A stoichiometric amount of methyl isocyanate (29.5 milliliters, 0.50 mole) was then added in a slow stream subsurface over a period of 30 minutes at a temperature of 5° C.–12° C. with vigorous stirring. The mixture was stirred for an additional 45 minutes at a temperature of 10° C.–20° C. after which the reaction mixture was transferred to a Waring Blendor ® using water to flush out the resin kettle. The mixture was then blended at high speed for a period of 30 seconds to give uniformly small particles after which an additional 3.0 milliliters (0.05 mole) of methyl isocyanate was added as the mixture was blended at high speed for another 30 second period. The reaction temperature rose to 21° C. The reaction mixture was then transferred back into the glass resin kettle and 1.0 milliliter (0.02 mole) of methyl isocyanate was added with vigorous stirring at a temperature of 20° C. The mixture was then stirred for a period of 30 minutes after which 2.9 grams of phosphoric acid in 10 milliliters of water was added in a slow stream subsurface. The resulting solid product was filtered off on a sintered glass funnel to give 97.88 grams (wet weight) of a fine white powder. High pressure liquid chromatographic analysis (internal standard) indicated the following: 91.88 percent 2-methyl-2-(methylthio) propionaldehyde O-(methylcarbamoyl) oxime (87.9 percent yield based on aldicarb oxime) and 0.34 percent 2-methyl-2-(methylthio) propionaldehyde oxime; 12.66 percent water content was determined by Karl Fischer titration.

EXAMPLE 4

Into a jacketed blender-reactor similar to a Waring Blendor ® equipped with rotor blades, a pressure-equalizing dropping funnel with Teflon ® tube, a thermometer and a dry ice/acetone cooled condenser was added 66.5 grams (0.50 mole) of 2-methyl-2-(methylthio) propionaldehyde oxime and 266 milliliters of water. Because of heat generated by the blender motor, the rotor blades were used only in 10 second bursts. A paddle-type stirrer was inserted halfway into the blender and used continuously for agitation. After cooling the mixture to a temperature of 15° C. with a water/salt/ice bath, 0.3 grams (0.005 mole) of trimethylamine was added to the blender under a nitrogen atmosphere. An amount of methyl isocyanate slightly in excess of stoichiometric (32.4 milliliters, 0.55 mole) was then added over a period of 30 minutes at a temperature of 15° C. with vigorous stirring. The water/salt/ice bath was removed and the mixture was stirred for an additional 90 minutes. The water/salt/ice bath was then put back in place and 2.9 grams of phosphoric acid in 10 milliliters of water was added in a slow stream subsurface. The resulting solid product was filtered off on a sintered glass funnel to give 91.62 grams of a white powder. High pressure liquid chromtographic analysis (internal standard) indicated the following: 97.12 percent 2-methyl-2-(methylthio) propionaldehyde O-(methylcarbamoyl) oxime (93.7 percent yield based on aldicarb oxime) and 1.78 percent 2-methyl-2-(methylthio) propionaldehyde oxime; 1.10 percent water content was determined by Karl Fischer titration.

EXAMPLE 5

Into a 5-liter Morton flask equipped with an air-driven paddle stirrer, a pressure-equalizing dropping funnel, a thermometer and a dry ice/acetone cooled condenser vented through two traps to a caustic scrubber was added 319.7 grams (2.4 mole) of 2-methyl-2-(methylthio) propionaldehyde oxime, 1279 milliliters of water, 2.4 grams (0.024 mole) of triethylamine, 16.0 grams of SAG 10® antifoam (10 percent solution) available from Union Carbide Corporation, Danbury, Conn., and 0.4 grams of Pluronic L-61 surfactant available from BASF Corporation, under a nitrogen atomosphere. After cooling the mixture to a temperature of 8° C.–10° C. with a salt/water/ice bath, 143.8 grams (2.52 mole) of methyl isocyanate was added over a period of 35 minutes with vigorous stirring. At this time an additional 1.2 grams of Pluronic L-61 surfactant was added and the mixture was stirred for an additional period of 95 minutes at a temperature of 15° C.–25° C. The resulting solid product was filtered off on a sintered glass funnel to give 555.3 grams of a white powder. High pressure liquid chromatographic analysis (internal standard) indicated the following: 70.8 percent 2-methyl-2-(methylthio) propionaldehyde O-(methylcarbamoyl) oxime (86.2 percent yield based on aldicarb oxime), 4.7 percent 2-methyl-2-(methylthio) propionaldehyde oxime and 9.1 percent water.

Into a jacketed one liter reaction vessel equipped with an electric stirrer, a thermocouple, a condenser vented through two traps to a caustic scrubber, a sample port, four baffles and a Teflon ® tube for subsurface addition was added 640 grams of water and 4.0 grams of Pluronic L-101 surfactant. After cooling the mixture to a temperature of 2° C.–3° C., 160.0 grams (1.20 mole) of 2-methyl-2-(methylthio) propionaldehyde oxime was added to the reaction vessel under a nitrogen atmosphere. A slight excess stoichiometric amount of methyl isocyanate (82.0 grams, 1.44 mole) was then added in a slow stream subsurface over a period of 20 minutes at a temperature of 2° C.–11° C. with vigorous stirring. The mixture was then stirred for an additional 45 minutes at a temperature of 10° C.–12° C. The resulting solid product was filtered off on a sintered glass funnel to give 230.83 grams of a white powder. High pressure liquid chromatographic analysis (internal standard) indicated the following: 73.2 percent 2-methyl-2-(methylthio) propionaldehyde O-(methyl-carbamoyl) oxime (77.0 percent yield based on aldicarb oxime) and 8.1 percent 2-methyl-2-(methylthio) propionaldehyde oxime; 18.7 percent water content was determined by Karl Fischer titration.

EXAMPLE 6

Into a jacketed one liter reaction vessel equipped with an electric stirrer, a thermocouple, a condenser vented through two traps to a caustic scrubber, a sample port, four baffles and a Teflon ® tube for subsurface addition was added 160.0 grams (1.20 mole) of 2-methyl-2-(methylthio) propionaldehyde oxime and 4.0 grams of Pluronic L-101 surfactant. After cooling the mixture to a temperature of 2° C.–3° C., 640 grams of water was added to the reaction vessel under a nitrogen atmosphere. An amount of methyl isocyanate slightly in excess of stoichiometric (82.0 grams, 1.44 mole) was then added in a slow stream subsurface over a period of 20 minutes at a temperature of 2° C.–11° C. with vigorous stirring. The mixture was then stirred for an additional 40 minutes at a temperature of 5° C.–12° C. The resulting solid product was filtered off on a Buchner funnel to give 226.22 grams of a white powder. High pressure liquid chromatographic analysis (external standard) indicated the following: 74.0 percent 2-methyl-2-(methylthio) propionaldehyde O-(methylcarbamoyl) oxime (76.1 percent yield based on aldicarb oxime) and 7.4 percent 2-methyl-2-(methylthio) propionaldehyde oxime; 16.5 percent water content was determined by Karl Fischer titration.

EXAMPLE 7

Into a jacketed one liter reaction vessel equipped with an electric stirrer, a thermocouple, a condenser vented through two traps to a caustic scrubber, a sample port, four baffles and a Teflon ® tube for subsurface addition was added 640 grams of water and 4.0 grams of Pluronic L-101 surfactant. After the mixture was cooled to a temperature of 2° C.–3° C., 160.0 grams (1.20 mole) of 2-methyl-2-(methylthio) propionaldehyde oxime was added to the reaction vessel under a nitrogen atmosphere. An amount of methyl isocyanate slightly in excess of stoichiometric (82.0 grams, 1.44 mole) was then added in a slow stream subsurface over a period of 20 minutes at a temperature of 2° C.–11° C. with vigorous stirring. The mixture was then stirred for an additional 45 minutes at a temperature of 5° C.–12° C. The resulting solid product was filtered off on a Buchner funnel to give 230.83 grams of a white powder. High pressure liquid chromatographic analysis (external standard) indicated the following: 73.2 percent 2-methyl-2-(methylthio) propionaldehyde O-(methylcarbamoyl) oxime (77.0 percent yield based on aldicarb oxime) and 8.1 percent 2-methyl-2-(methylthio) propionaldehyde oxime; 18.7 percent water content was determined by Karl Fischer titration.

We claim:

1. A process for preparing 2-methyl-2-(methylthio) propionaldehyde O-(methylcarbamoyl) oxime which comprises reacting 2-methyl-2-(methylthio) propionaldehyde oxime with methyl isocyanate in the presence of an aqueous medium for a period sufficient to form 2-methyl-2-(methylthio) propionaldehyde O-(methylcarbamoyl) oxime.

2. the process of claim 1 in which the molar ratio of methyl isocyanate to 2-methyl-2-(methylthio) propionaldehyde oxime is from about 0.25:1 to about 2:1.

3. The process of claim 1 in which the molar ratio of 2-methyl-2-(methylthio) propionaldehyde oxime to water is from about 1:1 to about 1:50.

4. The process of claim 1 in which a catalyst is added to the reaction.

5. The process of claim 4 in which the catalyst is a tertiary amine or organotin catalyst.

6. The process of claim 4 in which the catalyst is triethylamine or trimethylamine.

7. The process of claim 4 in which the catalyst is present in an amount of from about 0.01 weight percent to about 1.0 weight percent based on the weight of methyl isocyanate and 2-methyl-2-(methylthio) propionaldehyde oxime.

8. The process of claim 1 in which the reaction temperature is from about 0° C. to about 30° C.

9. The process of claim 1 in which the aqueous medium is water.

10. The process of claim 1 in which the reaction period is from about 1 second or instantaneous to about 10 hours.

11. The process of claim 1 in which an organic or inorganic acid is added to the reaction.

12. The process of claim 11 in which the acid is phosphoric acid.

13. The process of claim 11 in which the acid is added in an amount sufficient to quench the reaction.

14. The process of claim 1 in which an antifoaming agent is added to the reaction.

15. The process of claim 14 in which the antifoaming agent is added in an amount of from about 0.0001 weight percent to about 1.0 weight percent based on the total weight of the reaction mass.

16. The process of claim 1 in which a surfactant is added to the reaction.

17. The process of claim 16 in which the surfactant is added in an amount of from about 0.0001 weight percent to about 1.0 weight percent based on the total weight of the reaction mass.

18. The process of claim 1 in which 2-methyl-2-(methylthio) propionaldehyde O-(methylcarbamoyl) oxime is recovered by filtration.

* * * * *